(12) United States Patent
Imasaka et al.

(10) Patent No.: US 6,224,732 B1
(45) Date of Patent: *May 1, 2001

(54) METHOD AND APPARATUS FOR SEPARATING PARTICLES

(75) Inventors: Totaro Imasaka, Fukuoka; Kazuo Isaka, Tokyo; Toshikazu Ohnishi, Machida; Takeshi Miyazaki, Ebina, all of (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/734,971

(22) Filed: Nov. 19, 1996

Related U.S. Application Data

(63) Continuation of application No. 08/268,543, filed on Jul. 6, 1994, now abandoned.

(30) Foreign Application Priority Data

| Jul. 8, 1993 | (JP) | 5-169195 |
| Jul. 8, 1993 | (JP) | 5-169196 |
| Jul. 8, 1993 | (JP) | 5-169199 |

(51) Int. Cl.[7] .............. C25B 9/00; C25B 11/00; C25B 13/00
(52) U.S. Cl. .......... 204/600; 356/345; 356/28.5; 356/349; 250/550
(58) Field of Search .............. 204/600; 356/349, 356/345, 28.5; 250/550

(56) References Cited

U.S. PATENT DOCUMENTS

| 4,576,916 | * | 3/1986 | Lowke et al. | 435/289 |
| 4,887,721 | | 12/1989 | Martin et al. | 209/579 |
| 4,940,330 | * | 7/1990 | Dupheide et al. | 356/28.5 |
| 5,100,627 | * | 3/1992 | Buican et al. | 422/108 |
| 5,133,844 | | 7/1992 | Stevens | 204/180.1 |
| 5,376,252 | * | 12/1994 | Ekström et al. | 204/299 R |
| 5,416,576 | * | 5/1995 | Westlake, III et al. | 356/246 |

FOREIGN PATENT DOCUMENTS 0556748  8/1993  (EP).

OTHER PUBLICATIONS

Chemistry Letters, No. 1, Jan. 1991 (pp. 469–472) "Spatial Pattern Formation, Size Selection, and Directional Flow of Polymer Latex Particles by Laser Trapping Technique", by Hiroaki Misawa, et al.

Optics Letters, vol. 16, No. 19, Oct. 1, 1991, "Pattern formation and flow control of fine particles by laser-scanning micromanipulation", pp. 1463–1465, by Keiji Sasaki, et al.

Analytical Chemistry, vol. 60, No. 17, Sep. 1, 1988, "Field–Flow Fractionation", pp. 959A–971A, by Karin D. Caldwell.

* cited by examiner

Primary Examiner—Dwayne C. Jones
Assistant Examiner—C. Delacroix-Muirheid
(74) Attorney, Agent, or Firm—Fitzpatrick, Cella, Harper & Scinto

(57) ABSTRACT

A dispersing medium containing plural types of particles is let to flow in a flow path formed in a flow cell. The flow cell is irradiated with interfering light to form interference fringes of a pattern of stripes. In another arrangement, light is two-dimensionally scanned at high speed so as to cross a flow in the flow path. The moving particles receive a braking force by the light gradient force whenever they pass through each irradiation light stripe. In that case, greater braking forces act on particles having larger sizes (or larger refractive indices) than on particles having smaller sizes (or smaller refractive indices). Accordingly, the particles receiving smaller braking forces pass through the irradiated position more rapidly, so that particles can be separated to flow in the order from the particles receiving smaller braking forces to the particles receiving greater braking forces.

2 Claims, 14 Drawing Sheets

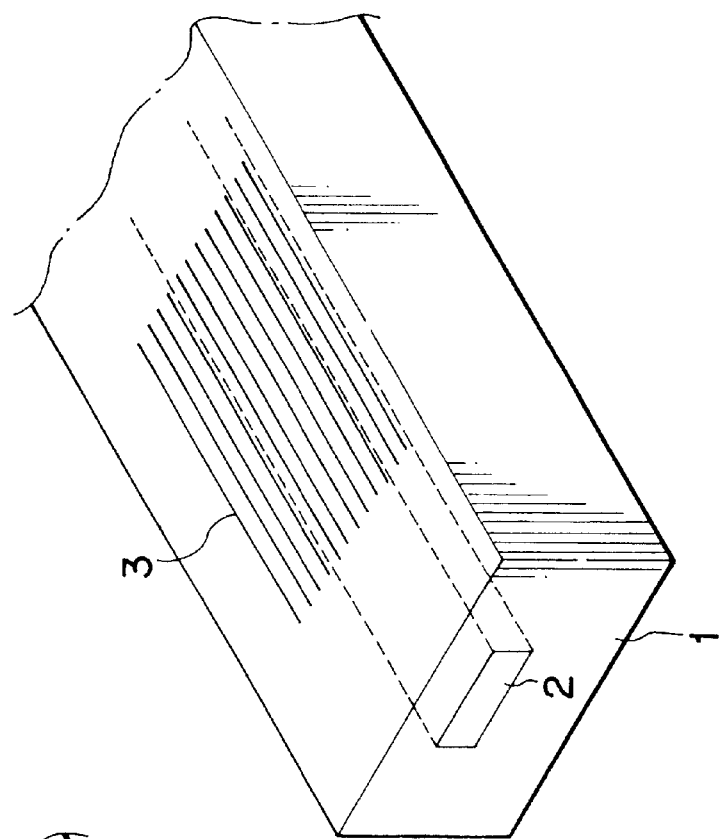
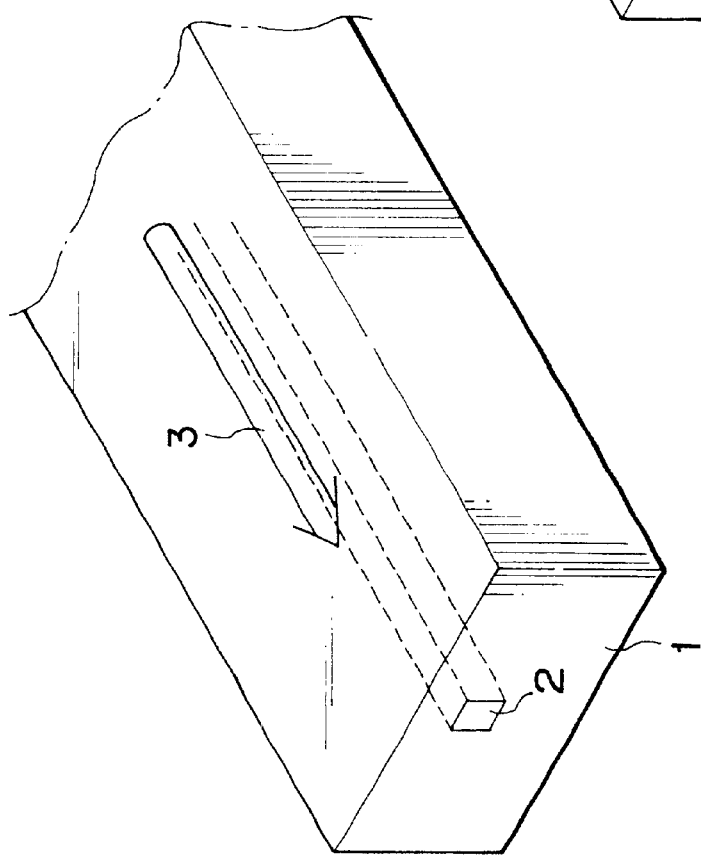
FIG. 8A
FIG. 8B

METHOD AND APPARATUS FOR SEPARATING PARTICLES

This application is a continuation, of application Ser. No. 08/268,543, filed Jul. 6, 1994, now abandoned.

BACKGROUND OF THE INVENTION

1. Field of the Invention

The present invention relates to technology for separating particles with light.

2. Related Background Art

Various methods have been known for separating particles such as living-organism-related particles, i.e., cells, microorganisms, liposomes, etc. and synthetic particles, i.e., latex particles, gel particles, industrial particles, etc.

As an example, there is a report on separating particles using so-called laser trapping, in which particles are confined in a space by collecting and condensing laser beams [H. Misawa, et al. Chem. Lett., 469(1991)].

The laser trapping is technology for handling the particles, utilizing a dynamic action of light on the particles. When a light beam having an intensity gradient, such as a laser beam, is condensed and irradiated onto particles, two types of forces act on the particles, i.e., a light pressure (a radiation pressure) acting in the irradiation direction of light beam and a force to confine the particles in the optical axis (i.e., a light gradient force). Either one of the light pressure and the light gradient force depends on the light intensity, an intensity distribution in the direction of the optical axis, which is a condensing degree by a lens and the like, and an intensity distribution in the direction perpendicular to the optical axis. The light pressure and the light gradient force further depend on the refractive index, the absorption index (reflectance) and the size of particles. Particles can be trapped at an irradiated position by the action of the gradient force among the two types of forces.

The separation of particles using the above-described laser trapping is conducted as follows. Prepared is a group of particles consisting of a mixture of two types of polystyrene latex particles which are different in size from each other. Laser beams are collected and condensed in a pattern of multiple rings by optical interference so as to impinge upon the particles. If the diameters of the rings are changed while keeping particles light-trapped on associated rings, smaller particles as weakly trapped spring out and are removed from the rings, whereby only larger particles are continuously trapped on the rings. As a result, the larger particles can be selectively separated.

SUMMARY OF THE INVENTION

However, the above-described method is insufficient in the separating ability, and it is difficult to separate, for example, three or more particle groups by the method.

The present invention has been accomplished to overcome the problem in the above-described conventional method. An object of the present invention is to provide a method and an apparatus achieving higher separating ability in a simple manner. According to one of preferred embodiments of the present invention to achieve this object, light is irradiated in a substantially stripe pattern onto moving particles to exert an acting force depending on the kind of particles, thereby effecting separation.

Further objects and preferred embodiments of the present invention will be clarified in the following description of the embodiments.

BRIEF DESCRIPTION OF THE DRAWINGS

FIG. 8A is a drawing to show a relation between a flow cell and scanning light in the fourth embodiment;

FIG. 8B is a drawing to show a relation between a flow cell and another scanning light in the fourth embodiment;

DETAILED DESCRIPTION OF THE PREFERRED EMBODIMENTS

Embodiment 1

Figure 2:
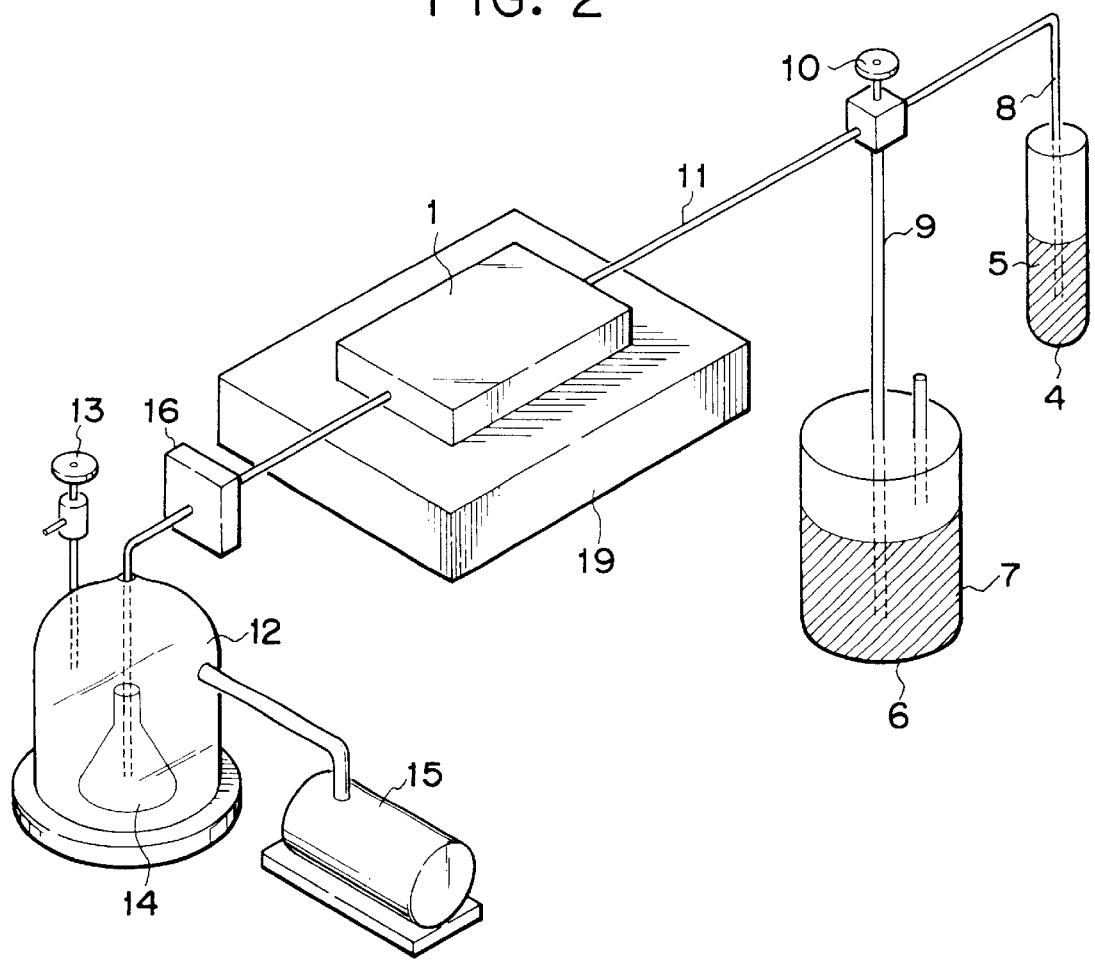
FIG. 2 is a drawing to show the structure of a fluid carrier system in an apparatus in the first embodiment.
Figure 3:
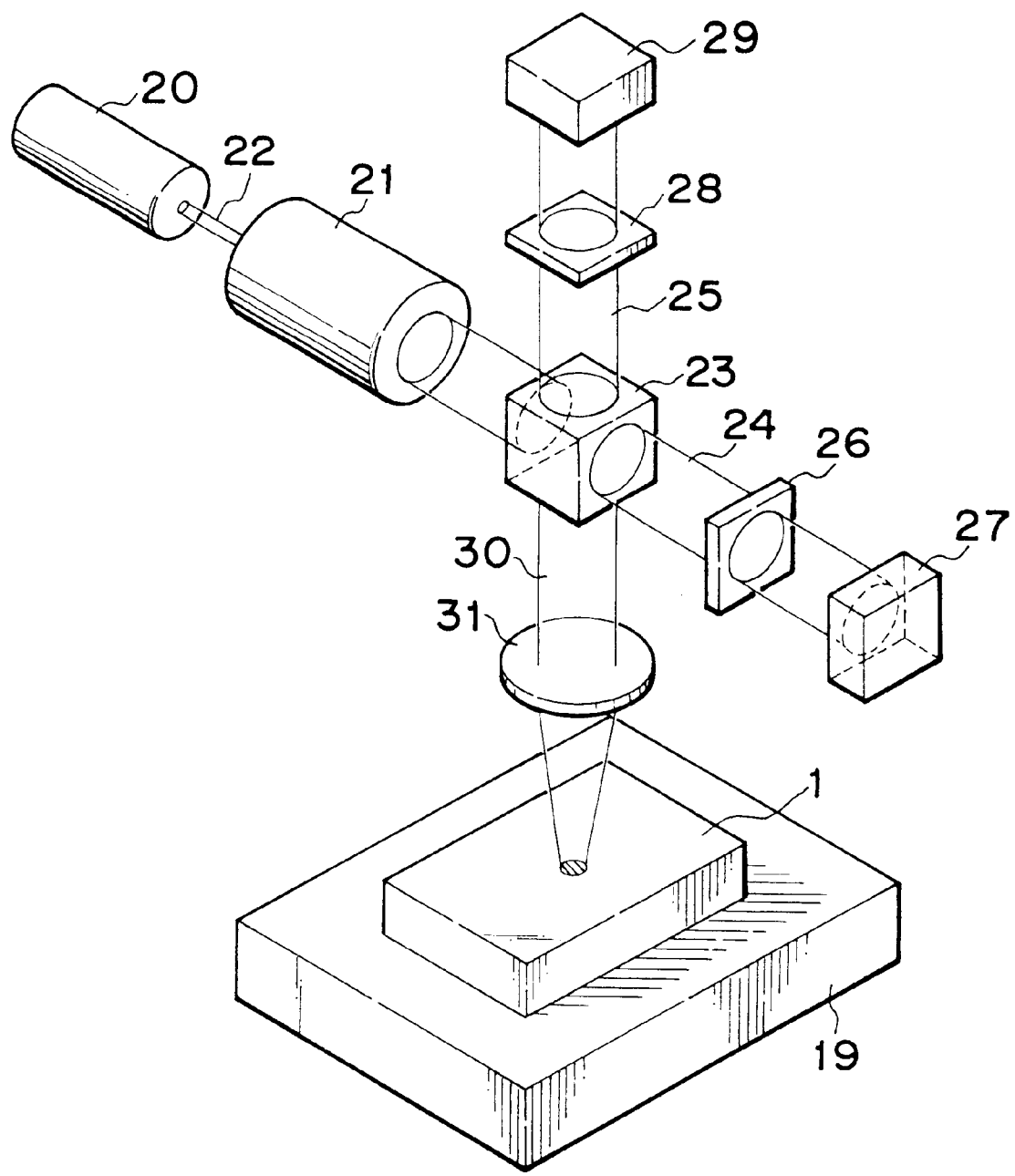
FIG. 3 is a drawing to show the structure of an irradiation optical system in the apparatus according to the embodiment.

The first embodiment of the present invention will be described with reference to the drawings. FIGS. 2 and 3 are drawings to show the overall structure of an apparatus in the present embodiment. FIG. 2 is a drawing to show the structure of a fluid carrier system in the apparatus of the present embodiment. In FIG. 2, the inside of a sample vessel 4 is charged with a particle-dispersed fluid 5 composed of plural (at least three) types of particles and a dispersing medium (e.g., water). In this case, the particles have the specific gravity at the same level as that of the dispersing medium. "Particles different from one another" in the present embodiment means that the particles are different from one another in either of (1) the size, (2) the refractive index and (3) the size and the refractive index. Specific examples of the particles include living-organism-related particles such as cells, viruses, microorganisms, liposomes, DNAs, and RNAs; synthetic particles such as latex particles, gel particles, industrial particles, and micelles; foreign particles such as dust; and soil particles.

A vessel 6 is charged with a dispersing medium 7 (for example, an aqueous solvent such as a buffer solution or an organic solvent such as ethanol). Tubes 8 and 9 are inserted into the sample vessel 4 and into the vessel 6, respectively, and these tubes are connected to a flow path 11 through a joint valve 10. The flow path 11 is connected to a flow cell 1 (supported on a stage 19) made of quartz glass and the flow cell 1 is connected to an exhaust chamber 12. The inside of the exhaust chamber 12 is kept hermetic by closing a valve 13. A separation vessel 14 is provided in the exhaust chamber 12 and a liquid flowing through the flow path is received in the separation vessel 14. In this arrangement, a suction pump 15 is activated to make the inside pressure in the exhaust chamber low so that a flow of the dispersing medium containing the particles can be formed in the flow cell 1. Particle measuring means 16, employing an optical (detection of scattered light and detection of fluorescence), electrical, magnetic or acousto-optic detection technique is provided downstream the flow cell 1.

FIG. 3 is a drawing to show the structure of an irradiation optical system in the apparatus in the present embodiment. In FIG. 3, reference numeral 20 denotes a light source. The wavelength of the light source 20 is preferably in the wavelength range in which light absorption by the particles is small, for example, in the wavelength range in which damage due to the light irradiation is minimum (as in the near infrared to infrared range) in case of living-organism-related particles such as cells. Specifically, a light source of TEM00 mode (Gaussian beam) laser, e.g., a solid laser such as YAG laser, a gas laser such as $Ar^+$ laser or a semiconductor laser, may be used. Further, any light source other than the laser light source may be used so long as it can produce light having the intensity gradient.

A light beam 22 emitted from the light source 20 is expanded by a beam expander 21 and then divided into two by a polarization beam splitter 23. The two divided beams 24 and 25 are sent back to the polarization beam splitter 23 by a reflection optical system composed of a quarter wave plate 26 and a reflecting mirror 27 arranged perpendicular to the optical axis and by a reflection optical system composed of a quarter wave plate 28 and a reflecting mirror 29 slightly inclined from a plane perpendicular to the optical axis, respectively. The two beams are mixed by the beam splitter 23 to form interfering light 30. Because the reflecting mirror 29 is slightly inclined, the interfering light 30 forms linear interference fringes repeating bright and dark portions at equal intervals. These bright and dark portions in the interference fringes have an intensity distribution in a shape of a sinusoidal wave. Further, the pitch and the direction of the bright and dark portions in the interference fringes can be controlled by adjusting the inclination angle and the inclined direction of the reflecting mirror 29.

Figure 1:
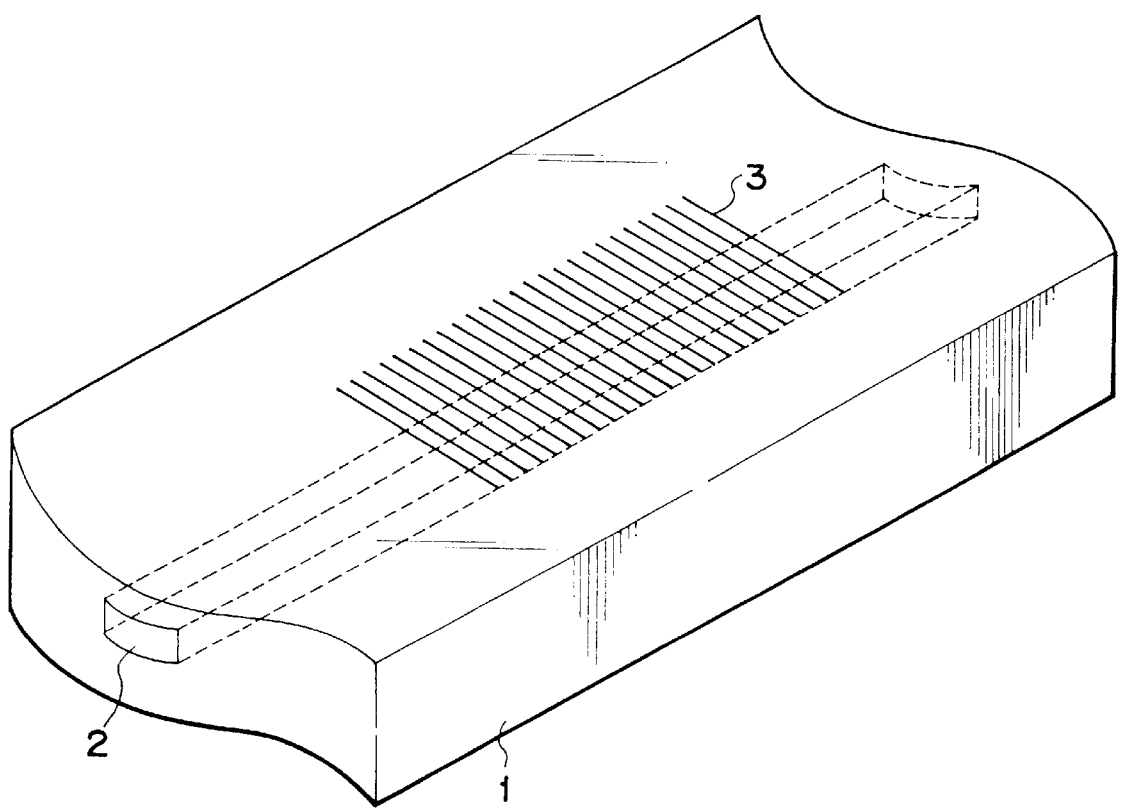
FIG. 1 is a drawing to show a state in which light is irradiated onto a flow cell.

The thus obtained interfering light 30 is irradiated through a lens system 31 onto the flow path in the flow cell 1. FIG. 1 is a drawing to show a state in which the flow cell 1 is irradiated with the light. The interfering light is so irradiated that the stripe-pattern interference fringes 3 cross the linear flow path 2. In the present embodiment, the angle made by the flow path and the interference fringes is 90°, but the angle is by no means restricted to 90°. The angle may be changed by inclining the flow cell 1 by the stage 19.

The apparatus of the present embodiment is so arranged that the irradiation intensity of the interfering light, which is emitted from the light source to impinge on the irradiation position, can be adjusted in order to set a threshold for separating the particles in accordance with the size or the refractive index. Specific examples of the adjustment may include (1) adjustment of the emission intensity of light from the light source, (2) adjustment of the irradiation amount by setting a modulating element or a filter in the optical path and (3) adjustment of the substantial irradiation amount by controlling an expansion rate of the lens system or the beam expander. Further, the threshold for separation of particles may be changed by controlling the wavelength of the interfering light.

Furthermore, the threshold or the separation resolution can also be set by adjusting the pitch of the bright and dark portions in the interference fringes by the interfering light. Specific examples of this adjustment may include (1) adjustment of the inclination angle of the reflecting mirror 29 and (2) changing of the incident angle of the irradiation light onto the flow cell 1 by the stage 19.

As described above, the separating conditions can be changed simply by varying the irradiation conditions of light, whereby the method and the apparatus of the present embodiment can flexibly be applied to separations of various types of particles.

The optical arrangement for forming the interference fringes is not limited to that as shown in FIG. 3. Many variations can be conceived. For example, it is possible that a beam from the light source is made obliquely incident onto a half mirror and that two branched beams are guided through different paths by respective mirrors and mixed to interfere with each other at the irradiated position. Another possible arrangement is such that a beam from the light source is made incident onto a grating and that plural diffraction beams generated thereby (for example, +first order light and −first order light) are guided through different paths by respective mirrors and mixed to interfere with each other at the irradiated position.

Further, interfering light to form interference fringes in a pattern of concentric circles may be used in addition to the interfering light to form interference fringes in a pattern of stripes. The interfering light of a pattern of concentric circles may be the Newton's rings or one obtained by arranging the reflecting mirror 29 as a convex mirror or a concave mirror.

Next described is the operation of the apparatus in the present embodiment. In FIG. 2, the joint valve 10 is turned to the tube 8 side and the particle-dispersed fluid in the sample vessel 4 is let to flow a little into the flow path 11. Then, the joint valve is changed over to the tube 9 side to let only the dispersing medium flow. As a result, the particles can flow on the flow of dispersing medium in the flow cell 1. At the irradiated position of the interfering light, a greater acting force (braking force) is exerted on particles having larger particle sizes (or larger refractive indices) as compared with particles having smaller particle sizes (or smaller refractive indices). Each of particles receives the braking force due to the light gradient force whenever it crosses a stripe in the interference fringes. Since the particles cross many interference fringes, the apparatus has an excellent separation ability. Accordingly, the particles receiving smaller braking forces pass through the irradiated position more rapidly, whereby the particles can be separated to flow in the order from the particles receiving smaller braking forces to the particles receiving greater braking forces.

The particles separated to flow are measured by the measuring means 16 and then received in a separation vessel 14. By changing the separation vessel 14 with another at an appropriate timing, the particles can be separately received every separated group of particles.

Embodiment 2

Figure 5:
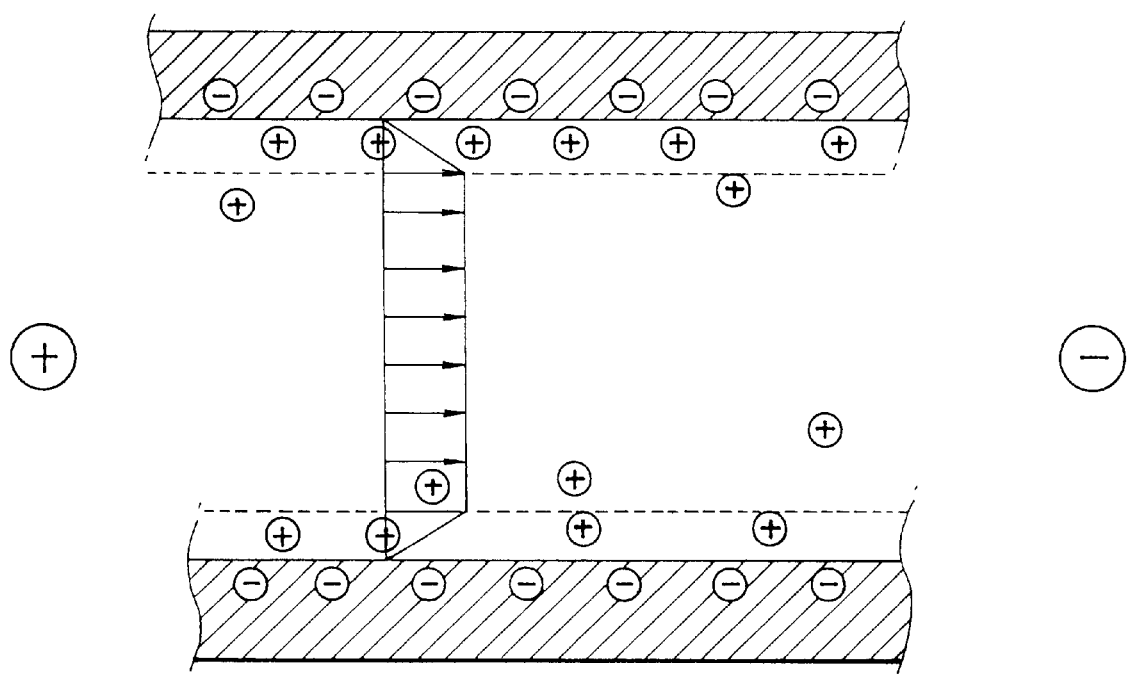
FIG. 5 is a drawing to illustrate a flowing state of fluid by an electroosmotic flow.

Next described is the second embodiment in which the fluid carrier system is different from that in the first embodiment. This embodiment is characterized in that an electroosmotic flow is utilized for transporting the fluid. Before describing this embodiment, the principle of the electroosmotic flow is explained with reference to FIG. 5.

Figure 6:
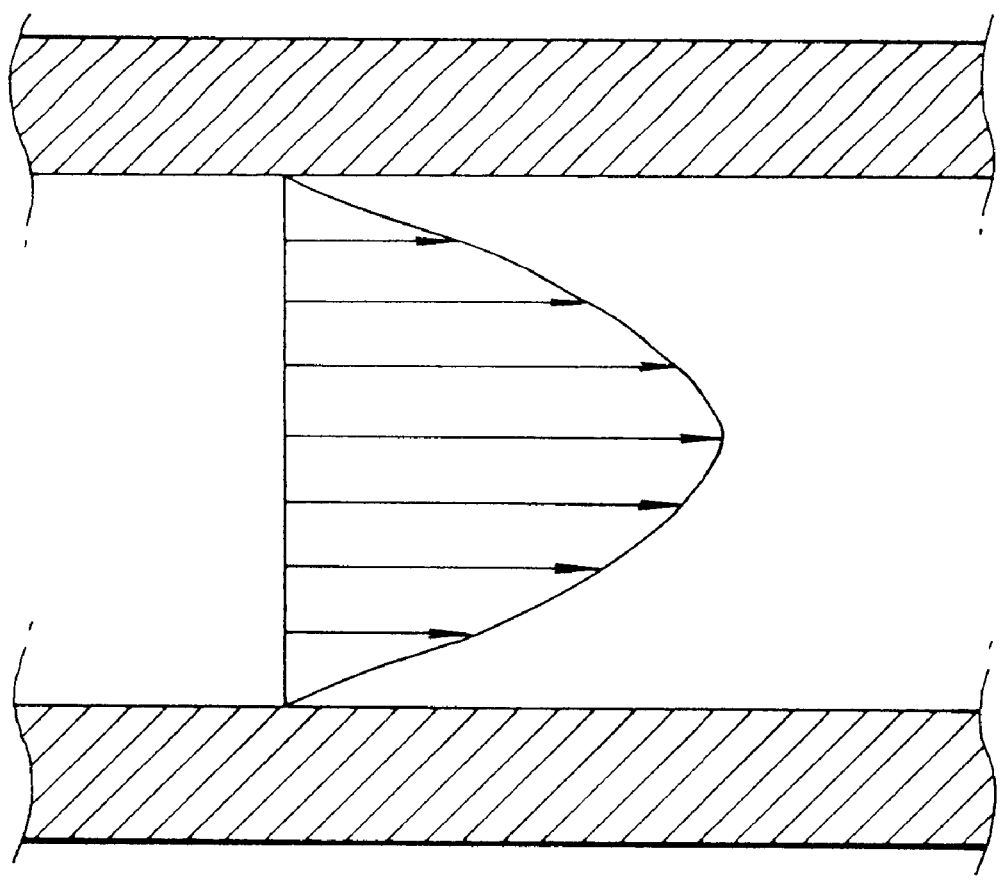
FIG. 6 is a drawing to illustrate a flowing state of fluid by pressure.

Walls in the flow path have negative electric charges fixed by ionization of silanol groups or the like. A solution in the flow path will have positive electron charges equivalent to the negative electron charges so as to neutralize them, whereby electric double layers are formed. Here, if an electric field is applied to the flow path in such a manner that a positive electrode is placed on the upstream side of the flow and a negative electrode on the downstream side of the flow, the positive electric charges receive a force because of the electric field and the whole solution moves toward the negative electrode. A velocity distribution of the electroosmotic flow in the flow path is almost uniform except for in the very vicinity of the electric double layers (the thickness of several angstroms), as shown by the arrows in FIG. 5, which is close to the plug flow. In case of the general method for transporting a liquid using water pressure, such as a pump, the flow velocity becomes faster as the position approaches the center of flow path, as shown in FIG. 6, different from the plug flow. Therefore, if the particles are separated using the electroosmotic flow, the separation ability can be considerably improved, because the liquid will have no disturbance.

Figure 4:
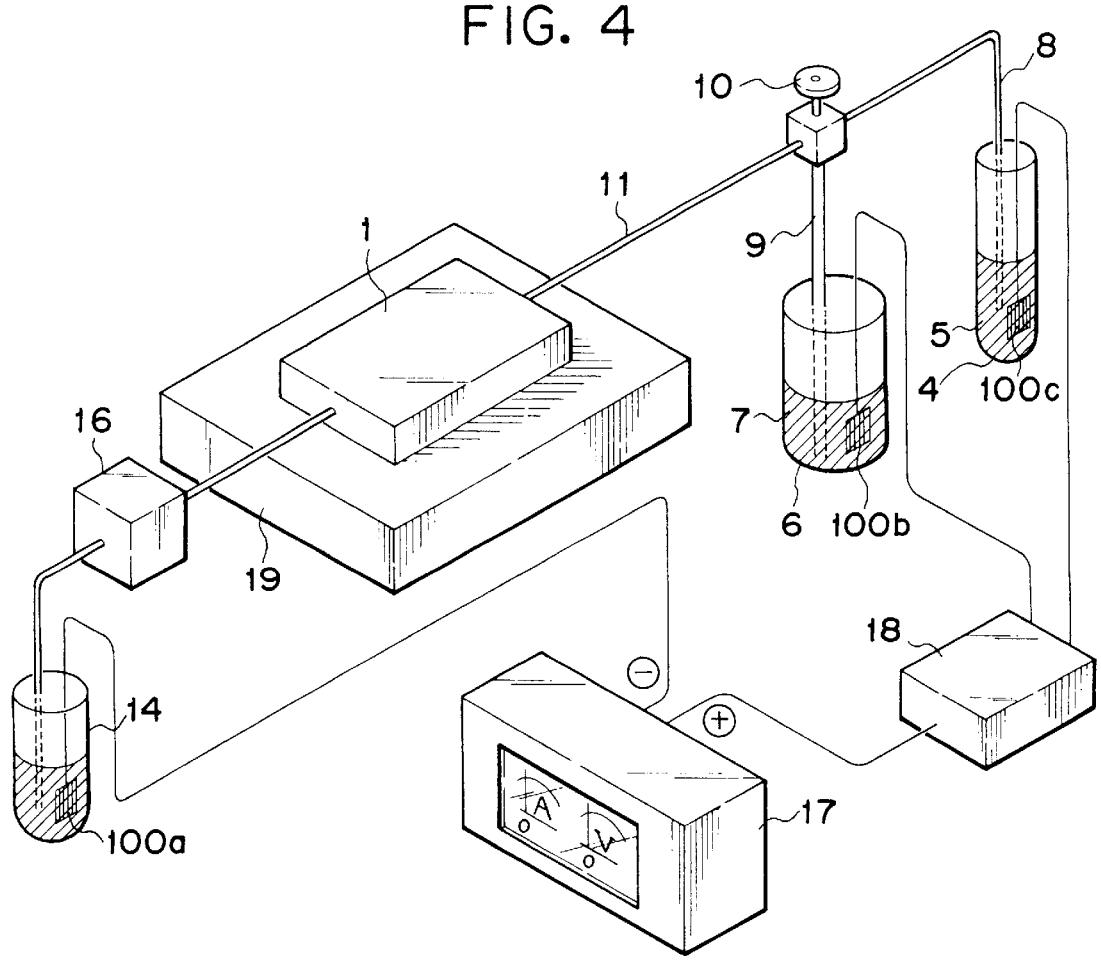
FIG. 4 is a drawing to show the structure of a fluid carrier system in the second embodiment.

Now, a fluid carrier system of the present embodiment is described with reference to FIG. 4. In FIG. 4, the same reference numerals as those in FIG. 2 represent the same constituents. Electrodes 100a, 100b and 100c are inserted into the separation vessel 14, the vessel 6 and the sample vessel 4, respectively, and immersed in respective liquids in the associated vessels. Each of these electrodes is connected to a high-voltage DC power source unit 17, so that the negative electricity is applied to the electrode 100a and the positive electricity is selectively applied to either electrode 100b or 100c through changeover of a relay 18.

The operation of the apparatus is described below. First, the joint valve 10 is turned to the tube 8 side and the high-voltage DC power source unit 17 is activated, whereby the positive electricity is applied to the electrode 100c provided in the sample vessel 4 and the negative electricity is applied to the electrode 100a provided in the separation vessel 14. An electroosmotic flow is generated by this operation in accordance with the principle as described above, and the particle-dispersed fluid 5 in the sample vessel 4 moves through the tube 8. When a little amount of the particle-dispersed fluid flows into the flow path 11 through the joint valve 10, the joint valve 10 is changed over to the tube 9 side and the positive electricity is applied to the electrode 100b in the vessel 6 through changeover of the relay 18. By this operation, only the dispersing medium 7 flows by the electroosmotic flow, so that the particles flow on the flow of dispersing medium in the flow cell 1.

As in the first embodiment, the flow cell 1 is irradiated with the interfering light and a greater acting force (e.g., a braking force) is exerted on particles having larger particle sizes (or larger refractive indices) as compared with particles having smaller particle sizes (or smaller refractive indices). Each of particles receives the braking force due to the light gradient force whenever it crosses a stripe in the interference fringes. Since these particles cross many interference fringes, the apparatus has an excellent separation ability. Accordingly, the particles receiving smaller braking forces pass through the irradiated position more rapidly, whereby the particles can be separated to flow in the order from the particles receiving smaller braking forces to the particles receiving greater braking forces.

Embodiment 3

The third embodiment of the present invention is described in the following. In this embodiment, light scan is performed in a direction to cross the flow path in the flow cell of a linear pattern.

Figure 7:
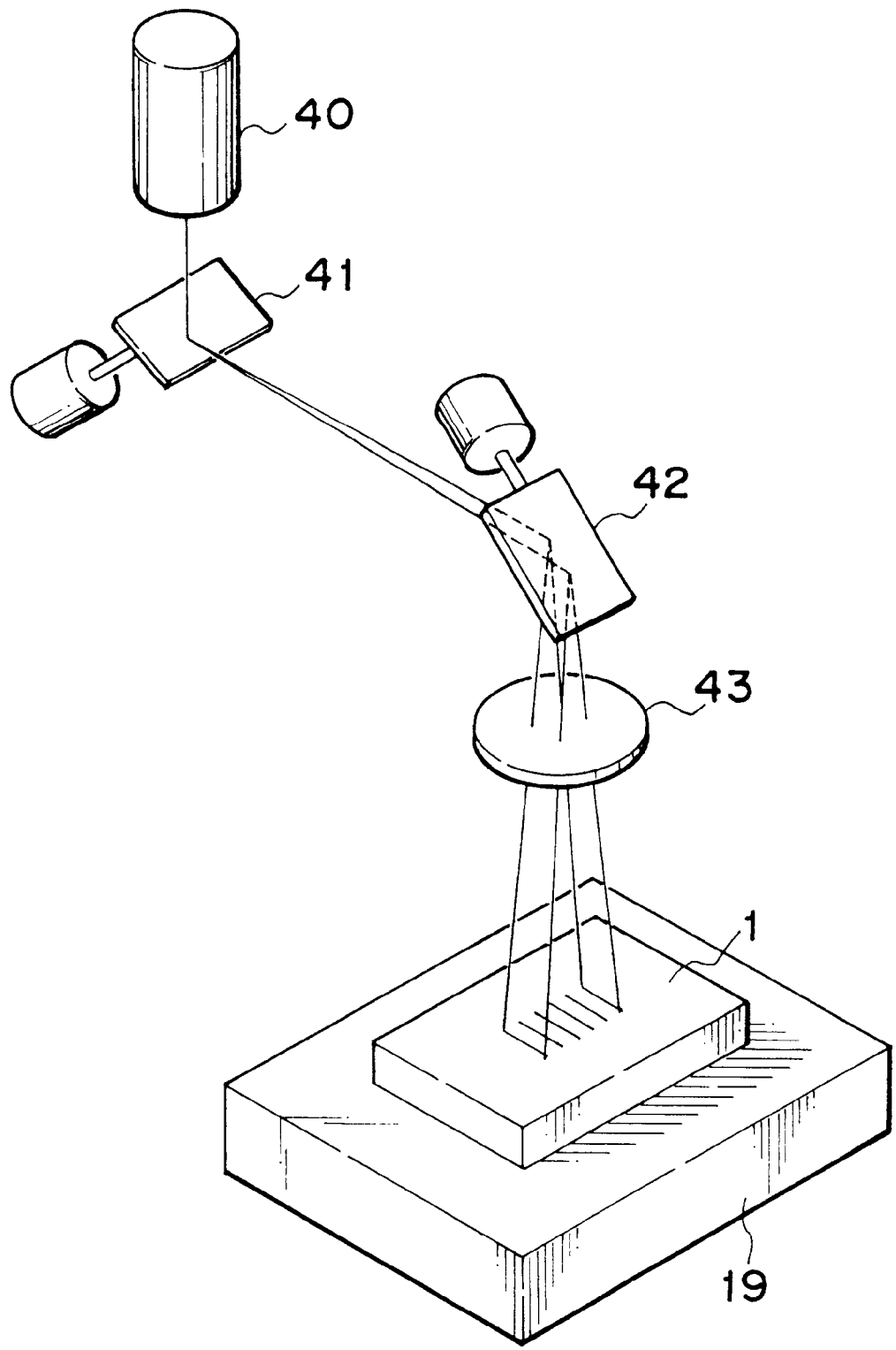
FIG. 7 is a drawing to show the structure of a scanning optical system in an apparatus in the third embodiment.

FIG. 7 is a drawing to show the structure of a scanning optical system in the apparatus of the present embodiment. In FIG. 7, reference numeral 40 denotes a light source. The wavelength of the light source 40 is preferably in the wavelength range in which light absorption by the particles is small, for example in the wavelength range in which damage due to the light irradiation is minimum (as in the near infrared to infrared range) in case of living-organism-related particles such as cells. Specifically, a light source of TEM00 mode (Gaussian beam) laser, i.e., a solid laser such as YAG laser, a gas laser such as Ar+laser or a semiconductor laser, may be used. Further, any light source other than the laser light source may be used so long as it can produce light having the intensity gradient.

A light beam emitted from the light source 40 is two-dimensionally deflected by two galvano-mirrors 41 and 42 to impinge on the flow cell 1 through a lens system 43, performing two-dimensional scan. It is noted that light-deflecting means other than the galvano-mirrors may be employed. For example, possible means may be a rotary polygon mirror, an acousto-optic element, or an electro-optical element. Further, the same light irradiation as that described above can be effected if the light scan is performed while moving the flow cell. In this case, the two-dimensional light scanning can be achieved on the flow cell by combining one-directional light-scanning means of one galvano-mirror with flow-cell-moving means of the stage 19.

The apparatus of the present embodiment is so arranged that the irradiation intensity of the scanning light, which is emitted from the light source to impinge on the irradiation position, can be adjusted in order to set a threshold for separating the particles in accordance with the size or the refractive index. Specific examples of the adjustment may include (1) adjustment of the emission intensity of light from the light source, (2) adjustment of the irradiation amount by setting a modulating element or a filter in the optical path and (3) adjustment of the substantial irradiation amount by controlling the lens system. Further, the threshold for separation of particles may be changed by controlling the wavelength of the scanning light.

Further, the threshold or the separation resolution can be set by adjusting the scanning pattern (the pitch or the scanning length) or the scanning speed through drive control of the scanning optical system.

As described above, the separation conditions can be changed simply by changing the light irradiation conditions, whereby the present invention can flexibly be applied to separation of various types of particles.

Next described is the operation of the apparatus in the present embodiment. The overall structure of the apparatus is the same as that shown in FIG. 2 or that shown in FIG. 4. Here, the operation is explained with reference to FIG. 2. The joint valve 10 is turned to the tube 8 side to let a little amount of the particle-dispersed fluid in the sample vessel 4 flow into the flow path 11. Then, the joint valve is changed over to the tube 9 side to let only the dispersing medium flow. Then, the particles flow on the flow of the dispersing medium in the flow cell 1. At the irradiated position of the scanning light, a greater acting force (e.g., a braking force) is exerted on particles having larger particle sizes (or larger refractive indices) than on the particles having smaller particle sizes (or smaller refractive indices). If the light scanning speed is set fully higher (for example, at least ten times higher) than the flowing speed of the particles through the flow cell, the light intensity on the scanning trace is substantially the same to the particles as that in the case where time-averaged steady light is irradiated. Thus, the particles receive the braking force because of the light gradient force whenever the particles cross a stripe in the light scanning trace. Since the particles cross many stripes in the scanning trace, the apparatus can have an excellent separation ability. Accordingly, the particles receiving smaller braking forces pass through the irradiated position more rapidly, whereby the particles can be separated to flow in the order from the particles receiving smaller braking forces to the particles receiving greater braking forces.

The particles separated to flow are measured by the measuring means 16 and then received in a separation vessel 14. By changing the separation vessel 14 with another at an appropriate timing, the particles can be separately received every separated group of particles.

Embodiment 4

The fourth embodiment of the present invention is next described. In the present embodiment, light scanning is performed along the flow path in the flow cell of a linear pattern.

FIGS. 8A and 8B are drawings to show a relation between the flow cell and the scanning light. In case the spot diameter of scanning light is substantially the same as or larger than the width of the flow path, one-dimensional light scanning is performed as shown in FIG. 8A. Further, in case the spot diameter of scanning light is smaller than the width of the flow path, two-dimensional light scanning is performed as shown in FIG. 8B. The light scanning speed is set fully higher than the flowing speed of particles as in the previous embodiment.

Figure 9:
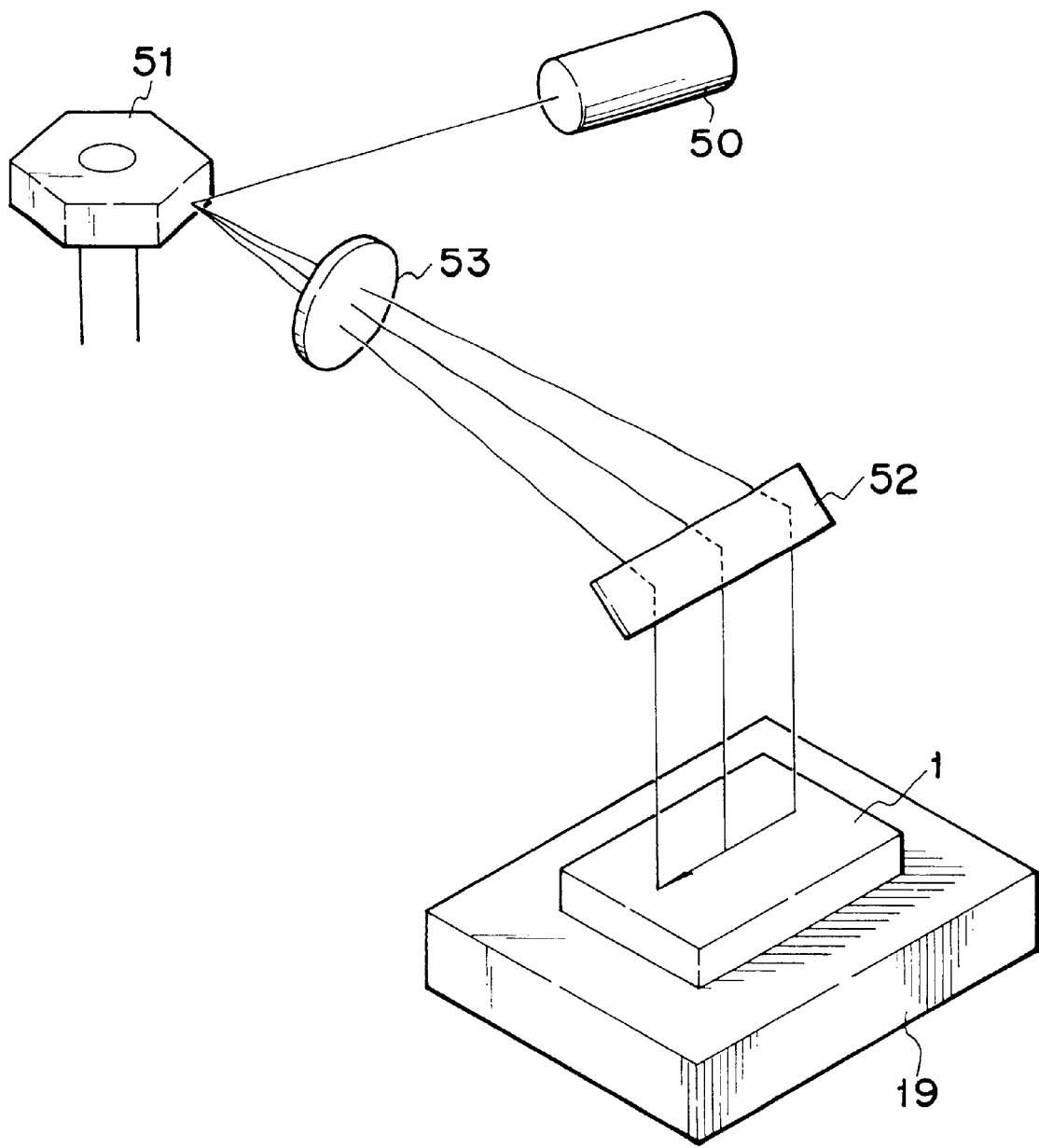
FIG. 9 is a drawing to show the structure of a scanning optical system in an apparatus in the fourth embodiment.

FIG. 9 is a drawing to show the structure of a scanning optical system for one-dimensional scanning. The fluid carrier system is the same as those in FIGS. 2 and 4, and description therefor is omitted. In FIG. 9, light from a light source 50 is deflected by a polygon mirror (rotary polygon mirror) 51 and irradiated onto the flow cell 1 through a reflecting mirror 52 and a lens system 53. Light scanning is performed only in one direction, i.e., in the opposite direction to the flowing direction of particles or in the same direction as the flowing direction of particles. Here, it should be noted that to and fro scanning is avoided. Since the light acts on the particles as a braking force in case of the scanning in the opposite direction, particles less affected by the dynamic action of light (particles with smaller sizes or smaller refractive indices) can pass sooner through the light-scanning region. On the other hand, in case of the scanning in the same direction, the light acts on the particles as a promoting force, so that particles more affected by the dynamic action (particles with larger particle sizes or larger refractive indices) can pass through the light scanning region more rapidly. As described, the direction of the acting force on the particles can be changed depending on the light scanning direction.

Embodiment 5

The fifth embodiment of the present invention is next described. The present embodiment is characterized in that a pattern of flow path in the flow cell is so arranged as to improve the separation ability for particles.

Figure 10:
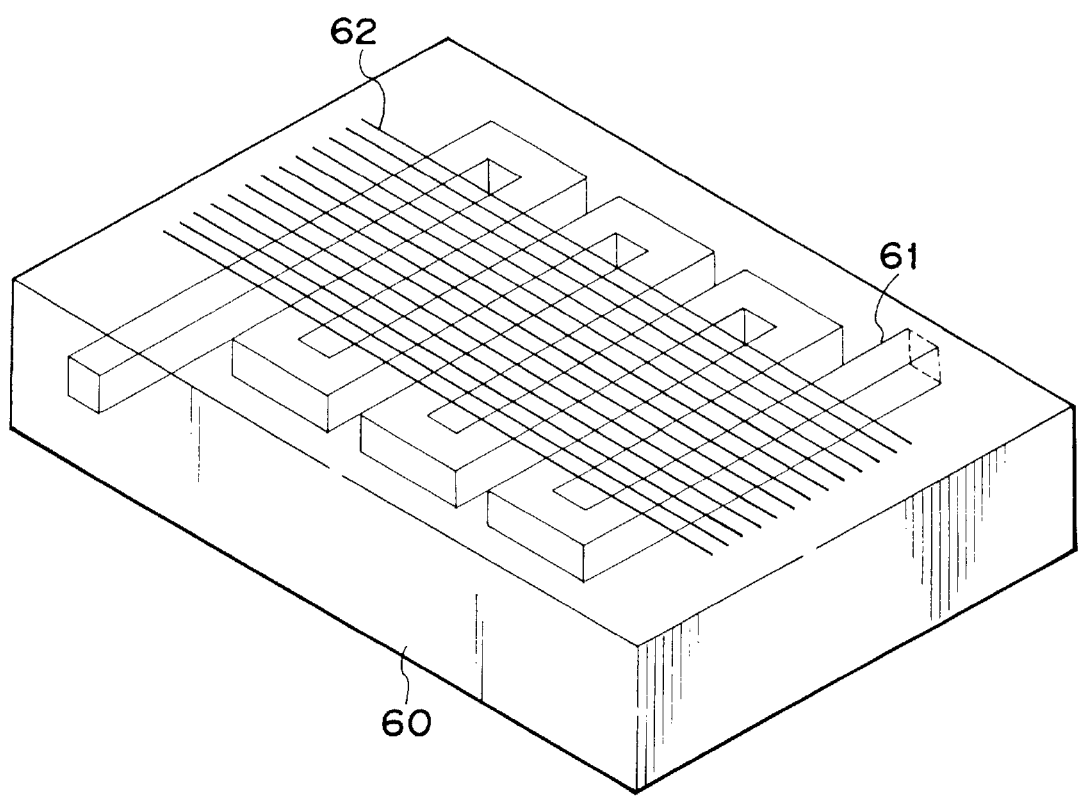
FIG. 10 is a drawing to show a relation between a flow cell and scanning light in the fifth embodiment.

FIG. 10 is a drawing to show a relation between the flow cell and the scanning light. The light is irradiated onto a flow path 61 of a folded path pattern formed in a flow cell 60, such that interference fringes of interfering light or scanning trace of scanning light crosses the flow as shown by reference numeral 62 in FIG. 10. Here, the fluid carrier system is the same as those shown in FIGS. 2 and 4 previously described. The flow cell having the fine flow path of such a folded path pattern can be produced by the micromachining technology.

According to the present embodiment, the acting force (e.g., a braking force) is exerted on the particles in plural regions along the flowing direction of the flow path 61, whereby separation can be effected in a high resolution, and, for example, at least three types of different particles can be readily separated. Further, since the flow path in flow cell is integrated in a fine region by the micromachining technology, a light irradiation region can be made small, which facilitates the designing of the interference optical system or the scanning optical system.

Figure 11A:
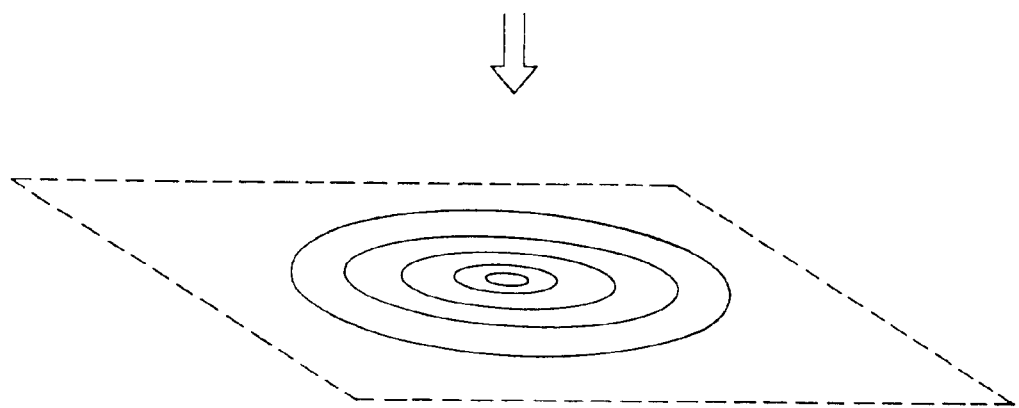
FIG. 11A is a drawing to show another arrangement of irradiation light.
Figure 11B:
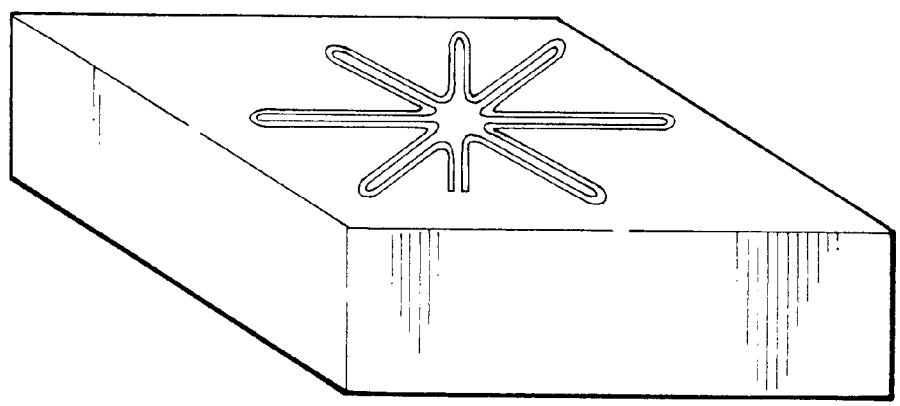
FIG. 11B is a drawing to show another pattern of flow path.
Figure 12A:
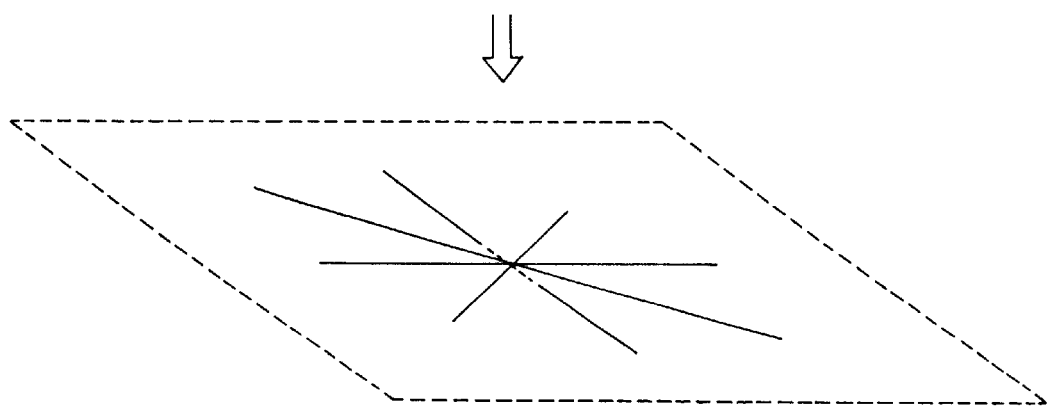
FIG. 12A is a drawing to show another arrangement of irradiation light.
Figure 12B:
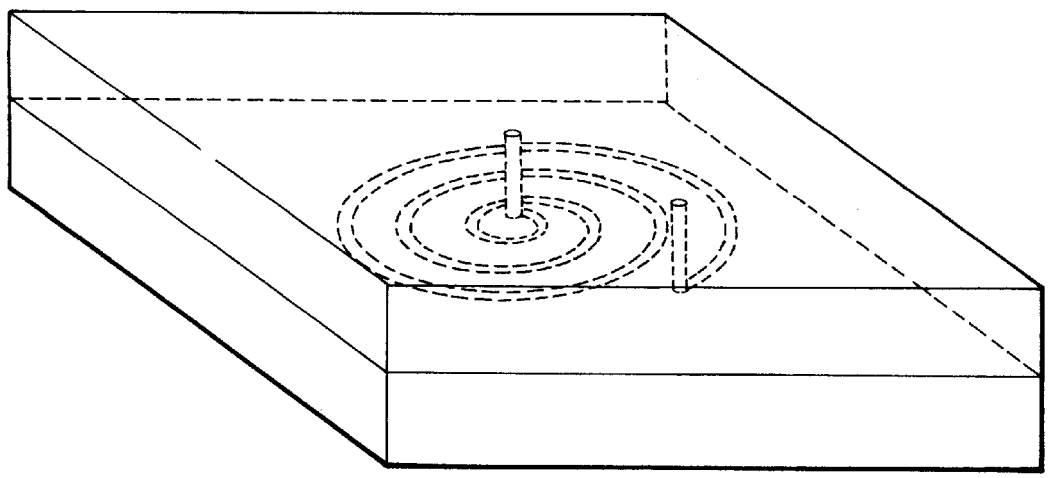
FIG. 12B is a drawing to show another pattern of flow path.

Further, instead of the folded path pattern of the flow path in flow cell as described above, a flow path of a radial pattern as shown in FIG. 11B or a spiral pattern as shown in FIG. 12B may be employed, onto which the light is irradiated in a pattern as shown in FIG. 11A or FIG. 12A, respectively.

Embodiment 6

Figure 13:
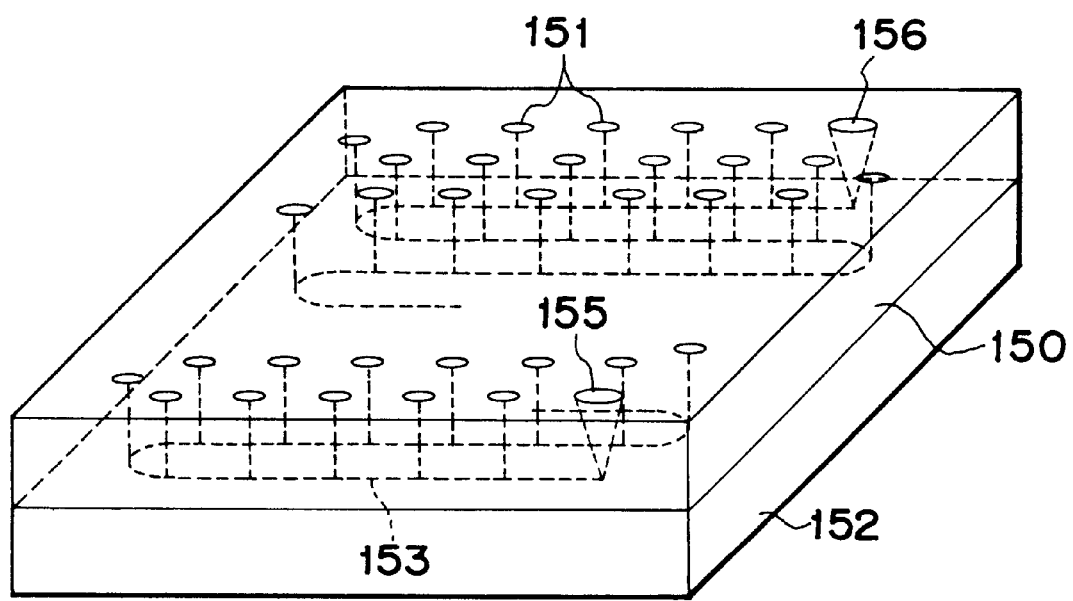
FIG. 13 is a drawing to show the structure of a flow cell in the sixth embodiment.

The sixth embodiment is next described. FIG. 13 is a drawing to show a perspective view of a flow cell used in the present embodiment. Reference numeral 151 represents a number of micro lenses formed on a substrate 150, and numeral 153, a flow path. The micro lenses 151 are formed along the flow direction in the flow path 153. Reference numeral 155 represents an inlet for dispersing medium connected to the flow path 153 and numeral 156 an outlet for dispersing medium therefrom.

When parallel light from an unrepresented light source is irradiated all over the upper surface of the flow cell, the irradiated light is converged by each of the micro lenses 151 at plural positions on the flow path 153. Particles in the dispersing medium flowing in the flow path 153 each receive the acting force (e.g., a braking force) because of the light gradient force at each converged position. The particles receive different braking forces depending on properties of the particles (the size or the refractive index), which in turn causes a difference in the flowing speed depending on the types of particles so as to effect separation.

Here, the pattern of the groove is not limited to the folded path pattern in the present embodiment, but may be the radial pattern or the spiral pattern as shown in FIG. 11B or FIG. 12B.

Figure 14A:
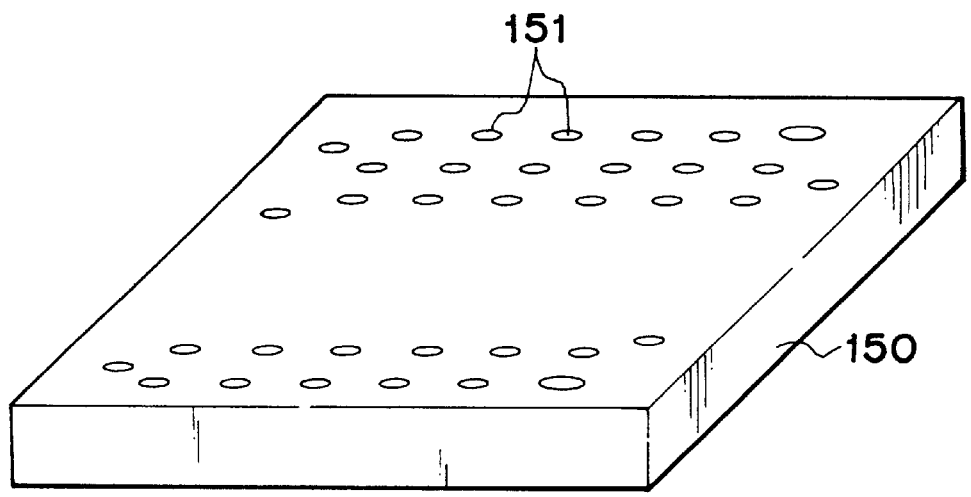
FIGS. 14A and 14B are drawings to illustrate a process for producing the flow cell in the sixth embodiment.

Next described is a method for producing the above flow cell. FIG. 14A is a drawing to show the structure of an upper substrate as a constituent of the flow cell. Reference numeral 150 is a transparent glass plate in the thickness of 0.5 mm, in which many micro lenses 151 are formed. Each micro lens has the diameter of 50 $\mu$m, which is produced in such a manner that ions, for example, of Ti are implanted into a porous glass by the photolysis method to form a refractive index distribution in the glass.

Figure 14B:
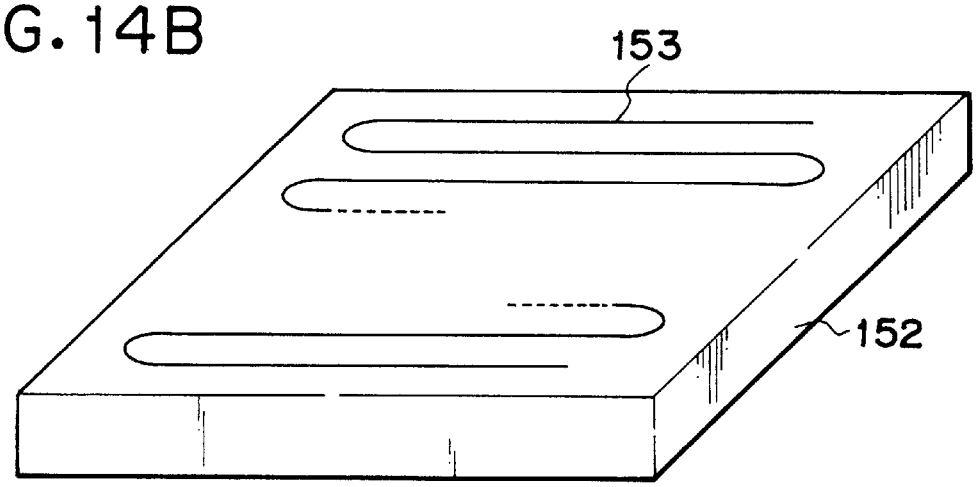

FIG. 14B is a drawing to show the structure of a lower substrate as another constituent of the flow cell. Reference numeral 152 represents a single crystal silicon substrate, on which a groove 153 to be a flow path is formed. A method for forming the groove 153 is as follows. The surface of the silicon substrate is coated with a photoresist by a spinner and exposure is effected by irradiating ultraviolet rays onto a portion to become the flow path, and thereafter removing the photoresist in accordance with the pattern of the flow path. Then, the groove 153 having the width of 10 $\mu$m and the depth of 10 $\mu$m is formed on the flow path portion by dry-etching such as the sputtering.

The glass substrate 150 in FIG. 14A and the silicon substrate 152 in FIG. 14B are overlaid precisely on each other such that the micro lenses match with the flow path. In this state, the lamination is placed on a heater and heated to 250° C. Then, a voltage of 200 V is applied to the both substrates to effect anode coupling between them. Instead, the anode coupling may be effected substantially at ordinary temperature by applying a voltage of 1 kV to the substrates while irradiating them with the $CO_2$ laser having the power of several watts/cm$^2$ from the side of the silicon substrate so as to prevent the ions in the micro lenses from thermally diffusing. A flow cell is thus obtained by the above procedures.

Here, the invention is not limited to such an arrangement that the glass plate and the single crystal silicon substrate are coupled to each other as described above. For example, such an arrangement may be employed for the flow cell that thin glass is bonded to a flow-path-formed surface of single crystal silicon to form a flow cell and that light is converged on the flow path through a separately provided glass plate having micro lenses. In this case, the glass plate having micro lenses can be set on the main body of the apparatus, whereby the flow cell can be advantageously provided at an inexpensive price.

What is claimed is:

1. An apparatus for separating particles, comprising:
   a flow path in which particles having various sizes and refractive indices move;
   means for generating an electroosmotic flow in said flow path; and
   optical means for irradiating said flow path with light of a substantially stripe pattern so as to apply braking force to the moving particles according to the sizes and the refractive indices of the particles, said optical means comprising a stripe pattern forming system forming the substantially stripe pattern at a portion where there is no branch of said flow path;
   wherein said flow path has a non-linear pattern.

2. An apparatus according to claim 1, wherein said flow path is folded plural times.

* * * * *

UNITED STATES PATENT AND TRADEMARK OFFICE
CERTIFICATE OF CORRECTION

PATENT NO. : 6,224,732 B1
DATED : May 1, 2001
INVENTOR(S) : Totaro Imasaka et al.

It is certified that error appears in the above-identified patent and that said Letters Patent is hereby corrected as shown below:

<u>Title page,</u>
Item [57], ABSTRACT,
Line 2, "let" should read -- allowed --.

<u>Column 1,</u>
Line 15, "etc." should read -- etc., --;
Line 26, "of light" should read -- of the light --; and
Line 46, "as weakly" should read -- which are weakly --.

<u>Column 2,</u>
Line 57, "and (3)" should read -- or (3) --.

<u>Column 3,</u>
Line 25, "as YAG" should read -- as a YAG --.

<u>Column 4,</u>
Line 41, "of dispersing" should read -- of the dispersing --;
Line 46, "of particles" should read -- of the particles --; and
Line 58, "received" should read -- received for --.

<u>Column 6,</u>
Line 11, "as YAG" should read -- as a YAG --; and "as Ar+laser" should read
-- as an Ar+laser --.

<u>Column 7,</u>
Line 13, "received" should read -- received for --;
Line 62, "trace" should read -- traces --; and "crosses" should read -- cross --.

<u>Column 8,</u>
Line 6, "in" should read -- in the --;
Line 12, "in" should read -- in the --;
Line 53, "tormed." should read -- formed. --; and
Line 61, "the sputtering" should read -- sputtering --.

UNITED STATES PATENT AND TRADEMARK OFFICE
CERTIFICATE OF CORRECTION

PATENT NO. : 6,224,732 B1
DATED : May 1, 2001
INVENTOR(S) : Totaro Imasaka et al.

It is certified that error appears in the above-identified patent and that said Letters Patent is hereby corrected as shown below:

Column 10,
Line 13, "path;" should read -- path, --.

Signed and Sealed this

Fourteenth Day of May, 2002

Attest:

JAMES E. ROGAN
Attesting Officer  Director of the United States Patent and Trademark Office